United States Patent
Ginggen et al.

(10) Patent No.: US 7,285,296 B2
(45) Date of Patent: Oct. 23, 2007

(54) PROCESS FOR ENRICHING EXTRACTS OF NATURAL THEANINE

(75) Inventors: Alec Ginggen, Muentschemier (CH); Yanik Tardy, Genevey/Coffrane (CH)

(73) Assignee: Medos S.A. (CH)

( * ) Notice: Subject to any disclaimer, the term of this patent is extended or adjusted under 35 U.S.C. 154(b) by 186 days.

(21) Appl. No.: 10/686,910

(22) Filed: Oct. 16, 2003

(65) Prior Publication Data
US 2005/0085763 A1    Apr. 21, 2005

(51) Int. Cl.
A61M 5/00 (2006.01)
A61M 25/00 (2006.01)
A61B 17/08 (2006.01)

(52) U.S. Cl. .......................... 424/729; 604/8; 604/264

(58) Field of Classification Search ............. 604/7–10, 604/264; 251/205–208, 118; 137/625.21, 137/247.19, 250, 487.5; 138/46; 606/153
See application file for complete search history.

(56) References Cited

U.S. PATENT DOCUMENTS

| | | | |
|---|---|---|---|
| 3,170,483 A | * | 2/1965 | Milroy .................. 137/553 |
| 3,949,966 A | * | 4/1976 | Fabish .................... 251/206 |
| 4,148,460 A | * | 4/1979 | Kinsler ................... 251/206 |
| 4,195,631 A | * | 4/1980 | Baucom ................. 604/6.04 |
| 4,615,691 A | * | 10/1986 | Hakim et al. .............. 604/9 |
| 4,904,236 A | * | 2/1990 | Redmond et al. .......... 604/9 |
| 5,192,265 A | | 3/1993 | Drake et al. |
| 6,095,491 A | * | 8/2000 | Kriesel ................... 251/206 |
| 6,264,625 B1 | * | 7/2001 | Rubenstein et al. ....... 604/9 |
| 6,394,980 B2 | | 5/2002 | Kriesell et al. |
| 2005/0055009 A1 | * | 3/2005 | Rosenberg .............. 604/500 |

FOREIGN PATENT DOCUMENTS

WO    WO9811934    3/1998

* cited by examiner

*Primary Examiner*—Michele Flood

(57) ABSTRACT

An adjustable resistance valve for a cerebrospinal fluid shunt system includes an actuator for allowing the selection of the resistance to flow of the valve, a device for selecting at least one passage traversing across the valve, and a resistance system. The resistance system includes a set of passages each defining a different resistance to flow. The passages are disposed in a circle facing the selecting device such as to guide the flow of the cerebrospinal fluid traversing the passage of the selecting device through the selected passage of the resistance system. The actuator enables one to change the relative position of the selecting device with respect to the resistance system by a rotational movement to select the desired resistance of the valve.

9 Claims, 2 Drawing Sheets

PROCESS FOR ENRICHING EXTRACTS OF NATURAL THEANINE

FIELD OF THE INVENTION

Figure 1A:
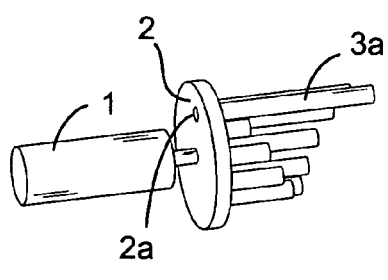

The present invention relates to an adjustable resistance valve adapted to be used within a shunt system for the treatment of hydrocephalus as well as a cerebrospinal fluid shunt system itself. Additionally, the present invention relates to a method of treatment of hydrocephalus using the adjustable resistance valve and to a method method of treatment of hydrocephalus using the cerebrospinal fluid shunt system.

DISCUSSION OF THE RELATED ART

In the ventricular system of the brain the so called cerebrospinal fluid (CSF) is formed at a given formation rate. This formation happens regardless of the intracranial pressure exerted on the brain by the cerebrospinal fluid, this latter normally being evacuated at a certain flow rate into the sagittal sinus as the natural CSF resorption site. In case of an obstruction along the natural cerebrospinal fluid pathway, which starts at the level of the ventricles of the brain situated in the middle of the cranium and ends in the sagittal sinus, the outflow of CSF from the ventricular system is reduced or completely interrupted leading to a pathological increase in the amount of cerebrospinal fluid located inside the cranium near its formation site. This pathological increase in the amount of intracranially located CSF or hydrocephalus causes an increase of the intracranial pressure, as the formation of CSF is widely independent of its evacuation.

Hydrocephalus is currently treated by either restoring the physiological CSF pathway by endoscopy, a method which can only be applied under certain conditions and which is limited in its success primarily by a high probability of re-obstruction of the natural pathway, or by derivation of the excess of CSF into a remote resorption site by using artificial means called shunt, thus restoring the normal physiological value of the intracranial pressure.

Such devices for the treatment of hydrocephalus by derivation of the excess of CSF are well known and make use either of resorption sites outside the cranium, by installing a shunt from the ventricular system of the brain to an adapted resorption site like the peritoneal cavity or the right atrium of the heart, or of the natural resorption site, the sagittal sinus, by trying to restore a pseudo-physiological pathway.

These devices primarily consist of three parts. A first part often called a proximal catheter is introduced in the ventricles of the brain and allows the draining of CSF from the ventricles. A second part called a distal catheter, which is usually similar in its realisation and functioning to the proximal catheter, is introduced in a distal resorption site like the atrium, the peritoneum or the sagittal sinus and allows drainage of CSF into the site. A third part, the main body of the shunt, is connected between the proximal and distal catheters and comprises means for regulating the drainage of CSF through the shunt, e.g. a valve or the like.

The method using other body cavities than the natural site as resorption site is the most commonly used one, the corresponding devices draining the CSF from the ventricles of the brain to the peritoneal cavity or to the right atrium of the heart, which have been found to be the most suitable diversion sites for CSF outside the cranium. For these kind of devices one knows several means regulating the flow of CSF through the shunt which primarily make use of one parameter, the pressure, amongst the several parameters one would consider to be important or convenient for the regulation process.

These regulating means can be classified in differential pressure valves and variable resistance valves. Differential pressure valves regulate the differential pressure across its ends, i.e. the difference of the pressure captured at the far ends of the catheters, some of these valves also permitting to select one of several possible values of the opening pressure of the valve non-invasively after implantation in order to allow a more flexible handling of the shunt. The main drawbacks of these devices are the so called siphoning effect and the unknown peritoneal pressure changes.

The first effect is due to hydrostatic pressure changes, e.g. when the patient changes position from the horizontal to the vertical position leading to a sudden increase in the hydrostatic pressure along the shunt. In that case, such a valve will open and drain most of the CSF of the ventricles of the brain until the pressure across the valve itself falls below its opening pressure. This inherits the danger of hyperdrainage leading to subnormal intracranial pressure. The patent U.S. Pat. No. 5,192,265 describes an example of a shunt trying to overcome these difficulties by proposing a rather complex anti-siphoning device allowing to select transcutaneously the resistance to flow by controlling the surrounding pressure of a channel having flexible walls.

The second effect is related to the fact that the shunt provides a connection between the ventricles of the brain and the peritoneum, the pressure of which being unknown. Therefore, it is impossible to anticipate the intracranial pressure, even if the opening pressure of the shunt is known, thus making it impossible for the surgeon to select the correct opening pressure a priori.

Variable resistance valves regulate the flow of CSF through the shunt by varying the resistance of the valve as a function of the distal pressure. These devices are in principle insensitive to the siphoning effect, but inherit the problem of necessitating access to atmospheric pressure. As the device is implanted, it makes it sensitive to subcutaneous pressure which is quite variable, and sensitive to the presence of scar tissues.

The other method for the treatment of hydrocephalus by artificial derivation of the excess of CSF consists in the installation of a shunt from the ventricular system of the brain to the natural resorption site, the sagittal sinus, the shunt then forming a pseudo-physiological pathway. This method was used less frequently in the past, but is nevertheless the object of current research. The document WO9811934 presents an overview of several existing devices in this field, it also explains the reasons for using the resistance to flow instead of the pressure as a parameter in a regulating device for a cerebrospinal fluid shunt. These reasons are primarily to avoid hyperdrainage of the ventricles of the brain by limiting the flow through the shunt and to allow to design a device reflecting the properties, especially the resistance to flow, of the natural CSF pathway. This document describes a device for the treatment of hydrocephalus having a fixed resistance to CSF flow which is designed to define a resistance similar to the normal resistance of the natural pathway from the ventricles of the brain to the sagittal sinus. Due to its fixed resistance the device cannot be fine tuned to the individual needs of a patient, i.e. after implementation it doesn't allow the surgeon to fit the resistance of the derivation circuit to match the resistance of the normal CSF resorption pathway of a specific pathway. Also, due to its very limited range in resistance to flow around 10 mm Hg/ml/min, the proposed device is limited to a treatment of hydrocephalus using the sagittal sinus as resorption site.

SUMMARY IF THE PRESENT INVENTION

The aim of the present invention is to remedy the inconveniences of the current systems by providing an adjustable resistance valve adapted to be integrated into a shunt system for the treatment of hydrocephalus, the resistance to CSF flow of the valve being adjustable non-invasively after implantation, the range of resistance to CSF flow covering the necessities of all possible resorption sites and the device being of simple construction.

Therefore, an object of the present invention is to provide an adjustable resistance valve for a cerebrospinal fluid shunt system including an actuator for allowing the selection of the resistance to flow of the valve. A device is provided for selecting at least one passage across the valve. A resistance system including a set of passages each defining a different resistance to flow is also included. These passages are disposed in a circle facing the selecting device, such as to guide the flow of the cerebrospinal fluid traversing the at least one passage of the selecting device through the selected passage of the resistance system. The actuator enables changing the relative position of the selecting device with respect to the resistance system by a rotational movement to select the desired resistance of the valve.

Another object of the present invention is to provide a cerebrospinal fluid shunt system incorporating an adjustable resistance valve having a proximal catheter to be introduced in the ventricles of the brain and allowing the draining of cerebrospinal fluid from the ventricles. A distal catheter is introduced in a distal resorption site such as the atrium, the peritoneum or the sagittal sinus and allowing drainage of cerebrospinal fluid into this site. A main body of the shunt is connected at one end to the proximal catheter and at the other end to the distal catheter. The main body houses an adjustable resistance valve comprising an actuator allowing the selection of the resistance to flow of the valve, with means for selecting at least one passage across the valve. The resistance system includes a set of passages each defining a different resistance to flow. The passages are disposed in a circle facing the selecting device such as to allow the flow of the cerebrospinal fluid traversing the at least one passage of the selecting device through the selected passage of the resistance system. The actuator enables changing the relative position of the selecting device with respect to the resistance system by a rotational movement to select the desired resistance of the valve.

A further object of the present invention is to provide a method of treatment of hydrocephalus using the adjustable resistance valve and a method of treatment of hydrocephalus using respectively the cerebrospinal fluid shunt system. The method of treatment of hydrocephalus includes:

implanting a cerebrospinal fluid shunt system into a patients cranium; and guiding the catheters to the chosen resorption sites.

BRIEF DESCRIPTION OF THE DRAWING FIGURES

The annexed figures represent, as an example, several embodiments of a device according to the invention.

Figure 1B:
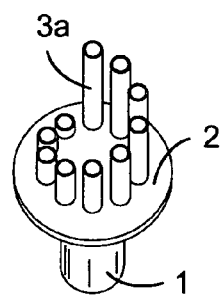
Figure 1C:
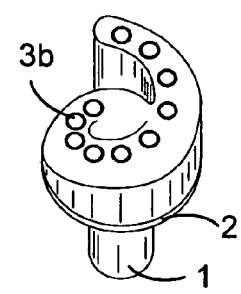

FIGS. 1a to 1c schematically illustrate the principle of two embodiments of an adjustable resistance valve for a cerebrospinal fluid shunt system according to the present invention.

Figure 2A:
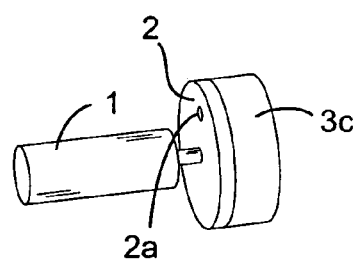
Figure 2B:
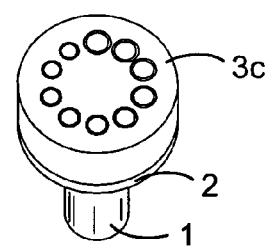

FIGS. 2a to 2b schematically illustrate the principle of another embodiment of an adjustable resistance valve for a cerebrospinal fluid shunt system according to the present invention.

Figure 3:
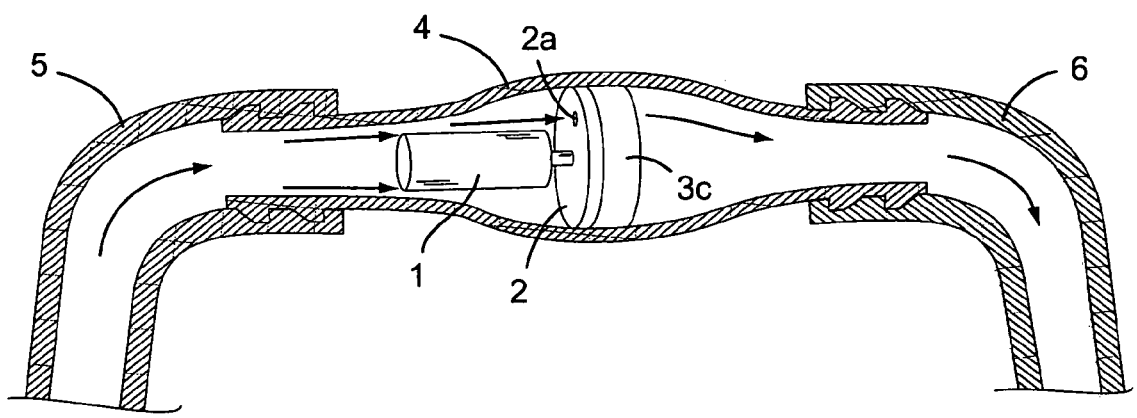

FIG. 3 is a schematic view of an adjustable resistance valve according to the present invention integrated in a cerebrospinal fluid shunt system.

Figure 4:
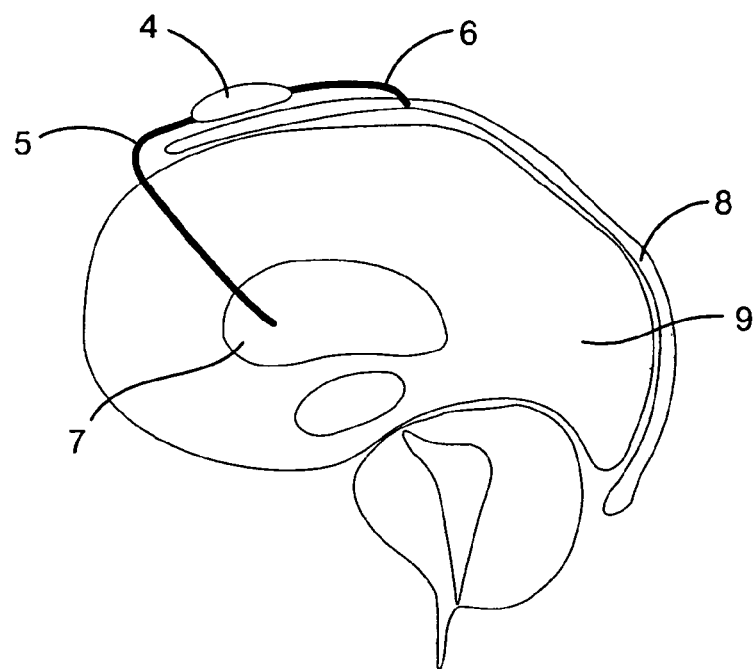

FIG. 4 schematically represents a cerebrospinal fluid shunt system disposed on the cranium.

DETAILED DESCRIPTION OF THE PRESENT INVENTION

The invention will now be described in detail with reference to the annexed figures which are illustrating by way of example several embodiments of the invention.

An adjustable resistance valve for a cerebrospinal fluid shunt system according to the present invention comprises, like illustrated in FIGS. 1a to 1c and 2a to 2b, an actuator 1 allowing the selection of the resistance to flow of the valve, and selecting means 2 with at least one passage 2a traversing these selecting means. A preferential realization of such selecting means is a disc 2 with at least one passage 2a traversing the disc near its periphery in a direction parallel to its longitudinal axis. Furthermore, an adjustable resistance valve according to the present invention comprises a resistance system 3 comprising a set of passages defining each a different resistance to flow, the passages being situated around a circle facing the selecting means 2 such as to guide the flow of the cerebrospinal fluid traversing the passage 2a of the selecting means 2 through the selected passage of the resistance system 3. In the above-mentioned case of a disc 2 as selecting means which will be used in the following explanations of the description for reasons of simplification, the passages of the resistance system 3 would preferentially be parallel to the axis of the disc 2. The disc 2, i.e. in general the selecting means 2, is adapted to be rotated by means of the actuator 1 in order to select the desired resistance of the valve by positioning the disc 2 such as to allow the flow of the cerebrospinal fluid traversing the passage 2a of the disc 2 through the selected passage of the resistance system 3. However, it is the relative position of the selecting means 2 with respect to the resistance system 3 which is important, thus it could as well be the resistance system 3 which is rotated with respect to the selecting means 2 by means of the actuator 1, this case not being explicitly illustrated in the figures. Thus, in general, the actuator 1 enables to change the relative position of the selecting means 2 with respect to the resistance system 3 by a rotational movement in order to select the desired resistance of the valve.

The actuator 1 comprises a motor connected to the disc 2 or to the resistance system 3 in order to drive the rotational movement of the disc 2 with respect to the resistance system 3, an energy source such as for example an antenna that can be coupled inductively to an external RF source or a battery, and corresponding electronics that will drive the motor, give feedback to the user about the actual relative position of the disc 2 with respect to the resistance system 3 and manage the energy consumption of the actuator.

The disc 2 comprises one passage 2a and is mounted such as to be able to turn in order to place the passage in the desired position for the selection of the required resistance to flow. Due to the reasons just mentioned, it could also be the resistance system 3 instead of the disc 2 which is mounted such as to be able to be rotated. The size of the passage 2a will be chosen such as not to limit the resistance of the passage with the smallest resistance to flow of the resistance system 3. As shown in FIGS. 1 and 2, the passage 2*a* is preferably situated at the periphery of the disc 2 in order to allow a geometrically favorable arrangement of the passages of the resistance system 3. However, it is also possible to equip the disc 2 with several passages situated on the disc 2 in a geometrically adequate manner, e.g. at a different radius from the center of the disc 2 and in correspondence to the arrangement of the resistance system 3, in order to allow a more efficient use of the available space, the disc 2 still allowing to choose a certain value of resistance to flow. The following description will, for reasons of simplicity, refer to the solution with one passage 2*a* in the disc 2 as depicted in the figures, without however limiting the scope of the invention.

The resistance system 3 itself comprises a set of passages corresponding to a set of resistances to flow. These resistances may be realized as shown in a first embodiment in FIGS. 1*a* and 1*b* by means of a set 3*a* of different tubes having each an identical internal diameter but a different length, these tubes being arranged parallel to each other, the openings disposed around a circle corresponding to the rotational movement of the passage of the disc 2. As shown in FIG. 1*c*, a second, functionally equivalent embodiment may consist of a body of essentially cylindrical shape 3*b* comprising a set of passages e.g. drilled into it and being disposed such as to form analogously a set of passages parallel to each other and to the axis of the body as well as to the axis of the disc 2, with the openings of the passages facing the rotational path of the passage of the disc 2. In order to obtain the different lengths of the passages of the body of cylindrical shape 3*b*, the body 3*b* comprises on its one end a recess of helicoidal shape, on the surface of which the passages depart.

The resistance system 3 may also be realized as a set of tubes disposed analogously to the one described in the first embodiment, the tubes however having all the same length, and in this case each a different internal diameter and forming thus a system of a variety of different resistances to cerebrospinal fluid flow. The same effect will be obtained by choosing an embodiment as depicted schematically in FIGS. 2*a* and 2*b*. Here, the set of tubes described above is simply replaced by a second disc or cylindrical body 3*c* comprising a set of passages having all the same length but each a different internal diameter, the passages being again disposed on a circular trajectory such as to face the rotational path of the passage of the disc 2.

The lengths, the internal diameters of the passages or tubes, respectively, of the resistance system 3 are chosen in such a manner as to define the total resistance to cerebrospinal fluid flow of the shunt system and to cover several discrete values reasonably distributed inside a range of resistance to flow of a 0-50 mm Hg/ml/min.

Thus, by turning the disc 2, the resistance to cerebrospinal fluid flow of the valve can be adjusted to a desired value. Apparently, this adjusting process can be done after implantation and non-invasively by means of the actuator 1 which will position the disc 2 such as to allow the cerebrospinal fluid to pass through the desired passage of the resistance system 3.

The surgeon has the possibility to adjust the resistance to flow of the valve non-invasively after implantation in order to optimally fit the patient physiology, thus allowing an optimal treatment of this pathology, and in order to match the resistance of the normal resorption pathway, and therefore the average cerebrospinal fluid flow rate, according to the resorption site of a specific case. This is especially facilitated by the large range of possible values for the resistance to flow of the adjustable resistance valve, like mentioned above.

The integration of such an adjustable resistance valve into a cerebrospinal fluid shunt system is schematically shown in FIG. 3. As mentioned above, these devices consist of three main parts. A main body 4 of the shunt houses the adjustable resistance valve. A proximal catheter 5 to be introduced in the ventricles of the brain and allowing the draining of CSF from the ventricles is connected at one end of the main body 4. A distal catheter 6 to be introduced in a distal resorption site like the atrium, the peritoneum or the sagittal sinus and allowing drainage of CSF into this site is connected at the other end of the main body 4.

The main body 4 thus serves as a housing for the regulating means realized by the above-mentioned valve, which regulates the flow of cerebrospinal fluid through the main body 4 according to the relative position of the disc 2 with respect to the resistance system 3. For this purpose, the disc 2 has to be arranged inside the main body 4 such as to allow its rotation but to exclude any fluid to pass elsewhere than through the passage formed in the disc 2, for example by using an annular joint. The resistance system 3 will be housed next to the disc 2 in such a way as to allow the fluid exiting from the passage 2*a* of the disc 2 to pass only through the selected passage of the resistance system 3, the cylindrical body 3*c* being for example in direct contact with the opposite surface of the disc 2 and the walls of the main body 4. The resistance system 3 may even be formed as a part of the main body 4, as well as the catheters 5 and 6, which are both parts well known to a person skilled in the art. Again, the previously mentioned inverse case of a fixed disc 2 and a resistance system 3 mounted such as to be rotated can be realized in a similar manner, too.

Moreover, a shunt system according to the present invention may comprise a check valve in order to avoid back flow of cerebrospinal fluid into the ventricles of the brain. These check valves being standard equipment of a shunt system, a variety of equivalent models may easily be integrated into a shunt system according to the present invention without modifying the scope of the invention.

Finally, FIG. 4 schematically shows a ventriculo-sagittal implantation of a shunt system according to the present invention. The proximal end of the catheter 5 is located in the ventricles 7 of the brain 9 and crosses the cranium through a first burr hole. The distal catheter 6 is tunneled under the skin to a second burr hole that allows access to the sagittal sinus 8. The main body 4 with the adjustable resistance valve is located between the two burr holes as well as between the skin and the cranium bone.

A corresponding method of treatment of hydrocephalus using the adjustable resistance valve as described above or the corresponding cerebrospinal fluid shunt system by implanting the device into a patient's cranium and guiding the catheters to the chosen resorption sites can be performed using this information.

An adjustable resistance valve and a shunt system, respectively, according to the present invention is intended for use as a derivation from the ventricles of the brain to different distal resorption sites such as the sagittal sinus, the right atrium of the heart or the peritoneum. The surgeon has the possibility to adjust the resistance to flow of the valve non-invasively after implantation in order to match the resistance of the normal resorption pathway, and therefore the average cerebrospinal fluid flow rate, and in order to optimally fit the patient physiology, thus allowing an optimal treatment of hydrocephalus.

The invention claimed is:

1. An adjustable resistance valve for a cerebrospinal fluid shunt system comprising:
   an actuator allowing the selection of the resistance to flow of the valve;
   means for selecting only one passage across the valve; and
   a resistance system comprising a set of passages each defining a different resistance to flow, the passages being disposed in a circle facing said selecting means, such as to guide the flow of the cerebrospinal fluid traversing said one passage of the selecting means through the selected passage of the resistance system, said actuator enabling to change the relative position of the selecting means with respect to the resistance system by a rotational movement to select the desired resistance of the valve, at least one of the lengths and the internal diameters of the passages are chosen in such a manner as to define the total resistance to cerebrospinal fluid flow of a corresponding shunt system and to cover a range of resistance to flow of 0-50 mm Hg/ml/min, the resistance system is a body of essentially cylindrical shape comprising a set of passages each having an identical internal diameter but a different length, the passages being disposed such as to form a set of passages parallel to each other and to the axis of the body, with the openings of the passages facing the rotational path of the passage of the selecting means, the body of essentially cylindrical shape comprising on its one end a recess of helicoidal shape, on the surface of which the passages depart, in order to obtain different lengths of the passages.

2. The valve according to claim 1, wherein the resistance system is a set of tubes each having an identical internal diameter but a different length, said tubes being parallel to each other, an opening of each tube being disposed in a circle corresponding to the rotational movement of the passage of the selecting means.

3. The valve according to claim 1 wherein the selecting means is a disc comprising at least one passage traversing the disc in a direction parallel to its longitudinal axis.

4. The valve according to claim 3 wherein the passages of the resistance system are parallel to said axis.

5. The valve according to claim 1 wherein the actuator comprises a motor connected to one of the selecting means and the resistance system in order to drive a relative rotational movement of the selecting means with respect to the resistance system; an energy source, and corresponding electronics that drive the motor, provide feedback to a user about the actual relative position of the selecting means with respect to the resistance system and manage the energy consumption of the actuator.

6. A cerebrospinal fluid shunt system comprising:
   a proximal catheter to be introduced in the ventricles of the brain and allowing the draining of cerebrospinal fluid from the ventricles;
   a distal catheter to be introduced in a distal resorption site such as the atrium, the peritoneum or the sagittal sinus and allowing drainage of cerebrospinal fluid into this site; and
   a main body of the shunt being connected at one end to said proximal catheter and at the other end to said distal catheter the main body houses an adjustable resistance valve comprising an actuator allowing the selection of the resistance to flow of the valve, means for selecting only one passage across the valve, and a resistance system comprising a set of passages each defining a different resistance to flow, the passages being disposed in a circle facing said selecting means such as to allow the flow of the cerebrospinal fluid traversing said one passage of the selecting means through the selected passage of the resistance system, said actuator enabling to change the relative position of the selecting means with respect to the resistance system by a rotational movement to select the desired resistance of the valve, at least one of the lengths and the internal diameters of the passages are chosen in such a manner as to define the total resistance to cerebrospinal fluid flow of the shunt system and to cover a range of resistance to flow of 0-50 mm Hg/ml/min, the resistance system is a body of essentially cylindrical shape comprising a set of passages each having an identical internal diameter but a different length, the passages being disposed such as to form a set of passages parallel to each other and to the axis of the body, with the openings of the passages facing the rotational path of the passage of the selecting means, the body of essentially cylindrical shape comprising on its one end a recess of helicoidal shape, on the surface of which the passages depart, in order to obtain different lengths of the passages.

7. A cerebrospinal fluid shunt system according to claim 6 wherein the main body is a housing for said valve, which regulates the flow of cerebrospinal fluid through the main body according to the relative position of the selecting means with respect to the resistance system, one of said selecting means and said resistance system being disposed inside the main body such as to allow its rotation but to exclude any fluid to pass elsewhere than through the passage formed in the selecting means and the selected passage of the resistance system.

8. A cerebrospinal fluid shunt system according to claims 6 further comprising a check valve in fluid communication with the main body for avoiding back flow of cerebrospinal fluid into the ventricles of the brain.

9. A method of treatment of hydrocephalus with a cerebrospinal fluid shunt system comprising a proximal catheter to be introduced in the ventricles of the brain and allowing the draining of cerebrospinal fluid from the ventricles, a distal catheter to be introduced in a distal resorption site such as the atrium, the peritoneum or the sagittal sinus and allowing drainage of cerebrospinal fluid into this site, and a main body of the shunt being connected at one end to said proximal catheter and at the other end to said distal catheter, said main body housing an adjustable resistance valve comprising an actuator allowing the selection of the resistance to flow of the valve, device for selecting only one passage across the valve, and a resistance system comprising a set of passages each defining a different resistance to flow, the passages being disposed in a circle facing with selecting device to allow the flow of the cerebrospinal fluid traversing the one passage of the selecting device through the selected passage of the resistance system, the actuator enabling changing the relative position of the selecting device with respect to the resistance system by a rotational movement to select the desired resistance of the valve, at least one of the lengths and the internal diameters of the passages are chosen in such a manner as to define the total resistance to cerebrospinal fluid flow of the shunt system and to cover a range of resistance to flow of 0-50 mm Hg/ml/min, the resistance system is a body of essentially cylindrical shape comprising a set of passages each having an identical internal diameter but a different length, the passages being disposed such as to form a set of passages parallel to each other and to the axis of the body, with the openings of the passages facing the rotational path of the passage of the selecting device, the body of essentially cylindrical shape comprising on its one end a recess of helicoidal shape, on the surface of which the passages depart, in order to obtain different lengths of the passages;

said method comprising the steps of:
  implanting a cerebrospinal fluid shunt system into a patients cranium; and
  guiding the catheters to the chosen resorption sites.

* * * * *

UNITED STATES PATENT AND TRADEMARK OFFICE
CERTIFICATE OF CORRECTION

PATENT NO. : 7,285,296 B2  Page 1 of 1
APPLICATION NO. : 10/686910
DATED : October 23, 2007
INVENTOR(S) : Alec Ginggen and Yanik Tardy It is certified that error appears in the above-identified patent and that said Letters Patent is hereby corrected as shown below:

On the cover page the title "PROCESS FOR ENRICHING EXTRACTS OF NATURAL THEANINE" should be changed to --ADJUSTABLE RESISTANCE VALVE FOR A CEREBROSPINAL FLUID SHUNT SYSTEM--

In Column 1, lines 1 to 2, the title "PROCESS FOR ENRICHING EXTRACTS OF NATURAL THEANINE" should be changed to --ADJUSTABLE RESISTANCE VALVE FOR A CEREBROSPINAL FLUID SHUNT SYSTEM--

Signed and Sealed this

Seventh Day of December, 2010

David J. Kappos
*Director of the United States Patent and Trademark Office*